United States Patent [19]

Haynes et al.

[11] 4,221,718

[45] Sep. 9, 1980

[54] PROCESS FOR PREPARING BENDIOCARB OF CRYSTALLINE FORM A

[75] Inventors: Harold G. Haynes, Foxton Royston; Robert W. Taylor, Cambridge, both of England

[73] Assignee: Fisons Limited, London, England

[21] Appl. No.: 43,100

[22] Filed: May 29, 1979

Related U.S. Application Data

[62] Division of Ser. No. 794,651, May 6, 1977.

[30] Foreign Application Priority Data

May 8, 1976 [GB] United Kingdom ............... 19019/76

[51] Int. Cl.² ........................................... C07D 317/46
[52] U.S. Cl. ............................................. 260/340.5 R
[58] Field of Search ................................. 260/340.5 R

[56] References Cited

FOREIGN PATENT DOCUMENTS 1220056 1/1971 United Kingdom ............. 260/340.5 R Primary Examiner—Ethel G. Love
Attorney, Agent, or Firm—Wenderoth, Lind & Ponack

[57] ABSTRACT

The pesticide 2,2-dimethyl-1,3-benzodioxol-4-yl N-methylcarbamate has been found to be capable of existence in several crystalline forms, which can be identified by their infra red spectra. The form commercially available has been form B but the new form A is superior.

26 Claims, No Drawings

PROCESS FOR PREPARING BENDIOCARB OF CRYSTALLINE FORM A

This is a division of application Ser. No. 794,651, filed May 6, 1977.

This invention relates to bendiocarb.

Bendiocarb, 2,2-dimethyl-1,3-benzodioxol-4-yl N-methylcarbamate, is a pesticide, particularly insecticide. It is usually formulated as a wettable powder and applied by spraying a dispersion of the wettable powder in water. We have now discovered an improved form of bendiocarb.

Accordingly, the invention provides bendiocarb of crystalline form A as defined herein.

The invention also provides a process for preparing bendiocarb of crystalline form A, which process comprises heating bendiocarb of any other crystalline form in the solid state at a temperature below its melting point.

The invention also provides a process for preparing bendiocarb of crystalline form A, which process comprises solidifying molten bendiocarb.

The invention also provides a process for preparing bendiocarb of crystalline form A, which process comprises holding any other crystalline form at a temperature of at least 35° C. in a liquid medium of such low solubility for bendiocarb that some bendiocarb is being dissolved while other is crystallising out of solution.

The invention provides in addition a process for preparing bendiocarb of crystalline form A, which process comprises recrystallising bendiocarb of any other crystalline form.

The invention also provides a process for preparing bendiocarb of which at least 85% by weight is of crystalline form A, which process comprises reacting methyl isocyanate with 2,2-dimethyl-4-hydroxy-1,3-benzodioxole at a temperature of at least 35° C. in a liquid medium in which the reactants dissolve at least partially but in which bendiocarb is substantially insoluble, and maintaining the resultant bendiocarb at a temperature of at least 35° C. in contact with the liquid medium until at least 85% by weight of the bendiocarb is of form A.

The invention in addition provides a pesticidal composition comprising bendiocarb in crystalline form A together with a carrier and/or surface active agent.

The invention further provides a method of combating pests at a locus infested or liable to be infested with them, which method comprises applying the pesticidal composition to the locus.

We have discovered that bendiocarb can exist in several crystalline forms, referred to as 'A', 'B', and 'C' herein. Form B has been commercially available in the United Kingdom and elsewhere, but form A is superior. When crystals of form B are stored, the crystals can grow, resulting in it being less satisfactory for mixing and application. Thus, a wettable powder containing it may not disperse as well in water or may not form as stable a suspension. Form A is surprisingly stable to storage.

We have found a test by which the various forms can rapidly and conveniently be distinguished, by examining the infra red spectrum. By the use of X-rays, it has been shown that the different forms are different crystalline forms. Mixtures of the forms also exist.

Crystalline forms A, B and C are defined as having an infra red spectrum substantially as indicated in the following table.

| WAVE-LENGTH, $CM^{-1}$ | A | B | C |
|---|---|---|---|
| 725 | TAIL OF 733 PEAK | PEAK | VERY LARGE PEAK |
| 733 | LARGE PEAK | TROUGH | |
| 741 | | TROUGH | |
| 756 | TROUGH | | PEAK |
| 768 | SMALL SHOULDER | PEAK | SMALL PEAK |
| 785 | VERY LARGE PEAK | PEAK/SHOULDER | PEAK |
| 795 | LARGE PEAK | VERY LARGE PEAK | LARGE PEAK |
| 805 | | TROUGH | |
| 1720 | | PEAK | |
| 1750 | PEAK | TAIL OF 1720 PEAK | SHOULDER (?) |
| 3330 | PEAK | TAIL OF 3370 PEAK | SHOULDER (?) |
| 3370 | TAIL OF 3330 PEAK | | PEAK |
| 3400 | TAIL OF 3330 PEAK | SHOULDER | TAIL OF 3370 PEAK |

Form A can be characterised by the peak at wavelength 733 $cm^{-1}$ or by the lack of a peak at 756 $cm^{-1}$. In a mixture of the forms, the percentage of each as referred to herein is as measured conventionally from the infra red spectrum. Thus, the fraction of form A in a mixture of forms can be measured as the fraction that the height of the peak at 733 $cm^{-1}$ on a log scale is to the same height given by the same total amount of bendiocarb but all in form A.

In both the identification of the various forms and measuring the amount of any particular form in a mixture of forms, the infra red spectrum is as obtained from a sample in the solid state using disc infra red analysis.

Form A can be produced by heating any other form at a temperature below its melting point. Thus, form A can be produced by heating form C at above 80°, preferably above 100°, but below its melting point. Temperatures in this specification are in degrees Centigrade. Form A can also be produced by heating form B at above 70°, preferably above 90°, but below its melting point.

Form A can also be produced by solidifying molten bendiocarb. Thus, any other form in the solid state, particularly form B, can be melted and then resolidified to form A.

Form A can also be produced by holding any other form at a temperature of at least 35° C. (usually at least 40°) in a liquid medium of such low solubility for bendiocarb that bendiocarb is dissolved from the material while other is crystallising out of solution. In this way the other form is gradually taken up into solution in the liquid medium and recrystallised out of solution as form A. The temperature may be at least 50°, preferably at least 60°. The temperature preferably is not more than 200°, especially not more than 180°, particularly not more than 160°, for instance not more than 85°. The time required may be for instance ¼–3 hours. Form B tends to be easier to convert in this way than form C.

Form A can also be produced by recrystallising any other form, e.g. form C. The liquid medium in which the other form is dissolved and then precipitated can be the same as that in the production of form A discussed above. The liquid medium may for instance have a boiling point in the range 100° to 200° but it is particularly preferred that the liquid medium be of boiling point in the range 115° to 200°, e.g. 120° to 180° especially 135° to 160°. Suitable as liquid medium is xylene, tetrachloroethylene, toluene, o-chlorotoluene, o-dichlorobenzene or cumene, preferably xylene, tetrachloroethylene, o-chlorotoluene, o-dichlorobenzene or cumene. Most preferred is cumene. The liquid medium may be a mixture of liquids but this is not preferred.

In a preferred procedure, bendiocarb is produced by reacting methyl isocyanate with 2,2-dimethyl-4-hydroxy-1,3-benzodioxole at a temperature of at least 35° (usually at least 40°) in a liquid medium in which the reactants dissolve at least partially but in which bendiocarb is substantially insoluble, and maintaining the resulting bendiocarb at a temperature of at least 35° (usually at least 40°) in contact with the liquid medium until at least 85% by weight of the bendiocarb is of form A. The reaction occurs in solution, but not all the hydroxy-benzodioxole need be dissolved at the start. Where it is not all dissolved at the start, as the reaction proceeds bendiocarb is precipitated and more hydroxy-benzodioxole dissolves. The reaction is usually carried out at 35° to 150° (usually 40° to 150°), and generally a catalyst is employed, usually a tertiary amine e.g. triethylamine or pyridine, or an organotin compound e.g. dibutyltin diacetate. Advantageously the temperature is 35° to 60°, e.g. 40° to 60°, and the pressure 1–1.1 atmospheres, e.g. ambient. The liquid medium can be the same as that in the production of form A discussed above. The liquid medium is preferably cumene or xylene. If the bendiocarb which precipitates initially is not form A or contains less form A than is desired, maintaining it in contact with the liquid medium at a temperature of at least 35°, usually at least 40°, preferably at least 50°, increases the percentage of form A as discussed above. The temperature is preferably not more than 200°, especially not more than 180°, particularly not more than 160°, for instance not more than 85°. A particularly preferred temperature is 58°–82°, e.g. 58°–62°. The time required for maintaining this contact may be for instance at least ¼ hour, usually at least 1 hour, preferably at least 2 hours, e.g. at least 3 hours. Preferably, the time is no more than 5 hours, e.g. no more than 3 hours. The time may be for instance ¼–3 hours. Preferably, the methyl isocyanate and the hydroxy-benzodioxole are admixed at a temperature of at least 40° and after the end of the admixing the reaction mixture is held at a temperature of 40°–85° (preferably 58°–82°) for at least 1 hour, preferably at least 2 hours, e.g. at least 3 hours. Most preferred is gradually adding the methyl isocyanate to a solution, or to a solution and suspension, of the 2,2-dimethyl-4-hydroxy-1,3-benzodioxole in the liquid medium, allowing the temperature to rise from 40° at the beginning of the addition to 60° at the end of the addition; then the temperature is preferably held at 58°–82°, for instance at 60°, e.g. for 3 hours. Advantageously of course one employs as short a time as provides consistent results in every run, depending on the particular conditions, e.g. choice of liquid medium, employed. All the present processes must of course be so operated, e.g. in their choice of liquid medium, temperature and time, as to obtain bendiocarb of the required form. In the present process, when the liquid medium is cumene a holding temperature of 58°–62° for 2 hours after mixing the reactants has been found consistently to give bendiocarb containing at least 95% by weight form A, whereas when the liquid medium is xylene a holding temperature of 78°–82° for 2 hours after admixing the reactants has been found consistently to give bendiocarb containing at least 95% by weight form A.

The present processes are usually conducted at a pressure of 0.5–10 atmospheres, conveniently at atmospheric pressure.

In a preferred embodiment, the invention provides bendiocarb at least 85% of which is of form A. Percentages in this specification are by weight. Preferably the bendiocarb is at least 90%, especially at least 95%, A.

Bendiocarb provided by the invention can be formulated in conventional ways with a carrier and/or a surface active agent. In particular, the bendiocarb can be mixed with a surface active agent with or, less preferably, without a solid carrier to form a wettable powder dispersible in water.

Solid carriers with which the bendiocarb may be incorporated include clays, sands, talc, mica or solid fertilizers, such products either comprising dust or larger particle size materials.

The surface active agents used may comprise anionic compounds such as soaps, fatty sulphate esters such as dodecyl sodium sulphate, octadecyl sodium sulphate and cetyl sodium sulphate, alkyl aromatic sulphonates such as fatty-alkyl benzene sulphonates or butyl naphthalene sulphonate, more complex fatty sulphonates such as the amide condensation products of oleic acid and N-methyl taurine or the sodium sulphonate of dioctyl succinate.

The surface active agents may also comprise nonionic surface active agents such as condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide. The surface active agents may also comprise cationic agents such as cetyl trimethylammonium bromide.

The present compositions may contain other pesticides in addition to bendiocarb, particularly other insecticides.

The present compositions are usually produced as concentrates, e.g. containing 0.5–85% of the bendiocarb, and these may be diluted, usually with water, for application by spraying, generally such that the concentration of bendiocarb is 0.02–3%. Thus, over all the compositions may contain 0.02–85% bendiocarb.

The compositions can be used to combat pests, particularly insects or acarids, in conventional ways.

The invention is illustrated by the following Examples, in which the amount of the various crystalline forms in the bendiocarb is as measured from the infra red spectrum.

EXAMPLE 1

Bendiocarb of form B was melted at 133° and then allowed to cool slowly, without forced cooling and without stirring. The product was bendiocarb consisting of 25% form A and 75% form C.

EXAMPLE 2

Bendiocarb of form B was melted at 133° and then cooled with stirring in cold water. The product was bendiocarb consisting of 70% form A and 30% form C.

EXAMPLE 3

20 g of bendiocarb form B was stirred at 60° in 40 ml xylene for ½ hour. The bendiocarb then contained more than 97% form A.

EXAMPLE 4

Bendiocarb form B was recrystallised from diethyl ether. The bendiocarb produced contained at least 95% form A.

EXAMPLES 5-7

Bendiocarb form B was recrystallised from cumene, (a) filtering off the product crystals at 90°, or (b) slowly cooling to ambient temperature, then filtering off the crystals, or (c) quickly cooling to ambient temperature with ice water, then filtering off the crystals. In each case the recrystallised bendiocarb contained at least 95% form A.

EXAMPLES 8-11

To a stirred mixture of 2,2-dimethyl-4-hydroxy-1,3-benzodioxole (100 gms) and cumene (200 mls) and a trace of triethylamine as catalyst was added a slight excess of methyl isocyanate over 2 hours, the temperature being maintained at $T_1°$ for the first hour and $T_2°$ for the second hour. The mixture was then kept at $T_3°$ for a further time H hours, cooled and filtered and the crystal form of the solid determined.

| Example | $T_1$ | $T_2$ | $T_3$ | H |
|---|---|---|---|---|
| 8 | 40 | 40 | 40 | 4 |
| 9 | 50 | 50 | 50 | 2 |
| 10 | 60 | 60 | 60 | 2 |
| 11 | 40 | 40 rising slowly to 60 | 60 | 3 |

In each case, the solid was bendiocarb form A.

EXAMPLE 12

Bendiocarb consisting of 81% form C and 19% form A was heated at 113° for 2 hours. The bendiocarb then contained 97% form A.

EXAMPLE 13

20 g of bendiocarb consisting of 67% form A and 23% form C were slurried at 60° in 70 ml cumene for ½ hour. The bendiocarb then contained 96½% form A.

EXAMPLE 14

20 g of bendiocarb consisting of 19% form A and 81% form C were slurried at 60° in 70 ml cumene. After ½ hour the bendiocarb contained 47% form A and after 1½ hours 97% form A.

EXAMPLE 15

Bendiocarb form B which was damp with cumene was heated at 70° for 17½ hours. The bendiocarb then contained 65% form A.

EXAMPLE 16

Bendiocarb form B was heated at 70° C. and the content of form A measured at intervals. Results were as follows:

| Time, hours | % form A |
|---|---|
| 0 | 0 |
| 17½ | 49 |
| 50 | 85 |
| 96 | 93½ |

The bendiocarb was then heated for 2½ hours at 110°. It then contained 99% form A.

EXAMPLES 17-21

80% Bendiocarb wettable powders were prepared by hammer milling, to a particle size under 50 microns Stokes equivalent diameter, a mixture of:
Bendiocarb, technical (97.4%)—82.1%
Precipitated Silica—9.9%
Mixture of anionic surface active agents—8.0%
The bendiocarb was as follows:

| Example | Bendiocarb |
|---|---|
| 17 | More than 97% A |
| 18 | 67% A, 33% C |
| 19 | 80% A, 20% B |
| 20 | 17% A, 83% B |
| 21 | 100% B |

EXAMPLES 22-24

80% Bendiocarb wettable powders were prepared by hammer milling, to a particle size under 50 microns Stokes equivalent diameter, a mixture of:
Bendiocarb, technical (97.4%)—82.1%
Diatomaceous Silica—9.9%
Mixture of anionic surface active agents—8.0%
The bendiocarb was as follows:

| Example | Bendiocarb |
|---|---|
| 22 | More than 97% A |
| 23 | 17% A, 83% B |
| 24 | 100% B |

EXAMPLES 25-32

The physical stability of the wettable powders of Examples 17-24 was measured in accelerated storage tests at suitable conventional temperatures, namely 40° and 54°.

The physical stability was measured by two tests, one a measure of the ease of mixing with water ('dispersibility'), the other a measure of the extent to which the particles, once well mixed with water, remain suspended (i.e. the conventional 'suspensibility' test).

For the 'dispersibility,' the measuring apparatus was a 2 liter straight-sided vessel, 60 cms long, with a 10 ml graduated centrifuge tube attached to the bottom.

11 grams of the wettable powder is added to the surface of 2 liters of a standard hard water (CIPAC 'D', see CIPAC Handbook Vol. 1, MT 18.1.4) at 30°±1° C. contained in a measuring cylinder. The cylinder is stoppered and inverted through 180° and back again three times during 15 seconds. The mixture is poured into the measuring apparatus and allowed to stand for 5 minutes. The less the volume of solid material now contained in the graduated tube, the better the dispersibility; 'good' samples will give less than about 1 ml of solid.

Suspensibility was measured by a conventional method, namely MT 15 in the CIPAC Handbook Vol. 1, 1970, using CIPAC water 'C' (ibid MT 18.1.3), the active ingredient being measured by gas liquid chromatography. The greater the suspensibility, the better.

The results are shown in the following Table, which for convenience also refers to the content of the various forms in the bendiocarb.

|  | FORMULATION I | | | | | FORMULATION II | | |
|---|---|---|---|---|---|---|---|---|
| EXAMPLE | 25 | 26 | 27 | 28 | 29 | 30 | 31 | 32 |
| Using Formulation of Example | 17 | 18 | 19 | 20 | 21 | 22 | 23 | 24 |
| Form of Bendiocarb | MORE THAN 97% A | 67% A 33% C | 80% A 20% B | 17% A 83% B | 100% B | MORE THAN 97% A | 17% A 83% B | 100% B |
| PROPERTIES OF FRESH FORMULATION | | | | | | | | |
| DISPERSIBILITY, MLS | 0.1 | 0.1 | 0.1 | 0.1 | 0.07 | 0.4 | 0.05 | 0.08 |
| SUSPENSIBILITY, % | 72 | 86 | 80 | 90 | 80 | 71 | 93 | 78 |
| AFTER 2 WEEKS AT 54° | | | | | | | | |
| DISPERSIBILITY, MLS | 0.4 | | 7 | >10 | >10 | 1.7 | >10 | >10 |
| SUSPENSIBILITY, % | 64 | 51 | 63 | | 8 | 71 | | 45 |
| AFTER 2 MONTHS AT 40° | | | | | | | | |
| DISPERSIBILITY, MLS | 0.3 | | | | 10 | | | |
| SUSPENSIBILITY, % | 65 | | 56 | | 48 | | | |

EXAMPLES 33–37

1 g mol (126 g) of pure grade pyrogallol was mixed with 1.125 g mols (117 g, 138 mls) of 2,2-dimethoxypropane and 525 mls of xylene (mixed isomers). The mixture was heated to boiling over 20 minutes, then distilled at 130 mls/hour (i) for 1 hour, adding xylene at the same rate and then (ii) for 4 hours, meanwhile adding 95 mls of xylene and pumping in below the liquid level 1.64 g mols of 2,2-dimethoxypropane. The residue (500 g) was distilled down to 413 g and found to contain, by analysis, negligible pyrogallol and 152 g, equivalent to a 92% yield, of 2,2-dimethyl-4-hydroxy-1,3-benzodioxole.

The residue was cooled to 45° C., a trace (½ ml) of triethylamine added, then in two lots, with cooling between, 1.1g mols of methyl isocyanate. After 4 hours agitation at 20°–25° C., isopropylamine (4 mls) was added to destroy the untreated methyl isocyanate. A sample of solid filtered off at 20–25° C. was found to be 100% form B. The remainder of the slurry was then stirred for time H hours at temperature T° C., cooled to 20°–25° C. and the form of the solid determined. The results are shown in the following Table:

| Example | 33 | 34 | 35 | 36 | 37 |
|---|---|---|---|---|---|
| T | 60 | 70 | 70 | 80 | 80 |
| H | 2 | ½ | 1 | 1 | 2 |
| Percent A in product | <5 | <10 | 57 | >95 | >95 |

We claim:

1. A process for preparing bendiocarb of crystalline form A, characterized by an infra red spectrum exhibiting a peak at wavelength 733 cm$^{-1}$ and a trough at wavelength 756 cm$^{-1}$, which process comprises heating bendiocarb of any other crystalline form in the solid state at a temperature below its melting point.

2. A process according to claim 1, wherein the bendiocarb prepared contains at least 85% by weight of crystalline form A.

3. A process according to claim 1, wherein the bendiocarb prepared contains at least 90% by weight of crystalline form A.

4. A process according to claim 1, wherein the bendiocarb prepared contains at least 95% by weight of crystalline form A.

5. A process for preparing bendiocarb of crystalline form A, characterized by an infra red spectrum exhibiting a peak at wavelength 733 cm$^{-1}$ and a trough at wavelength 756 cm$^{-1}$, which process comprises solidifying molten bendiocarb.

6. A process according to claim 5, wherein the bendiocarb prepared contains at least 85% by weight of crystalline form A.

7. A process according to claim 5, wherein the bendiocarb prepared contains at least 90% by weight of crystalline form A.

8. A process according to claim 5, wherein the bendiocarb prepared contains at least 95% by weight of crystalline form A.

9. A process for preparing bendiocarb of crystalline form A, characterized by an infra red spectrum exhibiting a peak at wavelength 733 cm$^{-1}$ and a trough at wavelength 756 cm$^{-1}$, which process comprises holding bendiocarb of any other crystalline form at a temperature of at least 35° C. in a liquid medium of such low solubility for bendiocarb that some bendiocarb is being dissolved while other is crystallizing out of solution.

10. A process according to claim 9, wherein the bendiocarb prepared contains at least 85% by weight of crystalline form A.

11. A process according to claim 9, wherein the bendiocarb prepared contains at least 90% by weight of crystalline form A.

12. A process according to claim 9, wherein the bendiocarb prepared contains at least 95% by weight of crystalline form A.

13. A process for preparing bendiocarb of crystalline form A, characterized by an infra red spectrum exhibiting a peak at wavelength 733 cm$^{-1}$ and a trough at wavelength 756 cm$^{-1}$, which process comprises recrystallising bendiocarb of any other crystalline form.

14. A process according to claim 13, wherein the bendiocarb prepared contains at least 85% by weight of crystalline form A.

15. A process according to claim 13, wherein the bendiocarb prepared contains at least 90% by weight of crystalline form A.

16. A process according to claim 13, wherein the bendiocarb prepared contains at least 95% by weight of crystalline form A.

17. A process for preparing bendiocarb of which at least 85% by weight is of crystalline form A, characterized by an infra red spectrum exhibiting a peak at wavelength 733 cm$^{-1}$ and a trough at wavelength 756 cm$^{-1}$, which process comprises reacting methyl isocyanate with 2,2-dimethyl-4-hydroxy-1,3-benzodioxole at a temperature of at least 35° C. in a liquid medium in which the reactants dissolve at least partially but in which bendiocarb is substantially insoluble, and maintaining the resulting bendiocarb at a temperature of at least 35° C. in contact with the liquid medium until at least 85% by weight of the bendiocarb is of crystalline form A.

18. A process according to claim 17, wherein the bendiocarb prepared contains at least 90% by weight of crystalline form A.

19. A process according to claim 17, wherein the bendiocarb prepared contains at least 95% by weight of crystalline form A.

20. A process according to claim 17, wherein the reaction is carried out in the presence of a tertiary amine as catalyst.

21. A process according to claim 17, wherein the methyl isocyanate and the hydroxy-benzodioxole component are admixed at a temperature of at least 40° C. and after the end of the admixing the reaction mixture is held at a temperature of 40°-85° C. for at least 1 hour.

22. A process according to claim 21, wherein after the end of the admixing the reaction mixture is held at a temperature of 58°-82° C. for at least 1 hour.

23. A process according to claim 17 wherein the liquid medium is of a boiling point in the range 115° to 200°.

24. A process according to claim 23, wherein the liquid medium is of a boiling point in the range 135° to 160°.

25. A process according to claim 17, wherein the liquid medium is xylene.

26. A process according to claim 17, wherein the liquid medium is cumene.

* * * * *